US005750551A

United States Patent [19]

Matsumori

[11] Patent Number: 5,750,551
[45] Date of Patent: *May 12, 1998

[54] TREATMENT FOR VIRAL DISEASES

[75] Inventor: Akira Matsumori, Osaka, Japan

[73] Assignee: Takeda Chemical Industries, Ltd., Osaka, Japan

[*] Notice: The term of this patent shall not extend beyond the expiration date of Pat. No. 5,105,919.

[21] Appl. No.: 736,593

[22] Filed: Dec. 24, 1996

Related U.S. Application Data

[62] Division of Ser. No. 200,686, Feb. 23, 1994, Pat. No. 5,605,919.

[30] Foreign Application Priority Data

Feb. 23, 1993 [JP] Japan ................................. 5-038234

[51] Int. Cl.⁶ ........................................................ A61K 31/41
[52] U.S. Cl. ........................... 514/381; 514/361; 514/364; 514/382; 514/394
[58] Field of Search ............................ 514/381, 361, 514/364, 382, 394

[56] References Cited

U.S. PATENT DOCUMENTS

| | | | |
|---|---|---|---|
| 4,216,313 | 8/1980 | Paget et al. | 544/55 |
| 4,420,479 | 12/1983 | Morwick et al. | 424/246 |
| 4,818,761 | 4/1989 | Sato et al. | 514/341 |
| 4,956,351 | 9/1990 | Mesens et al. | 514/58 |
| 5,294,720 | 3/1994 | Jadhav et al. | 546/265 |
| 5,310,740 | 5/1994 | Rosenberg et al. | 514/236.8 |
| 5,360,795 | 11/1994 | Townsend et al. | 514/43 |
| 5,605,919 | 2/1997 | Matsumori | 514/381 |

FOREIGN PATENT DOCUMENTS

| | | |
|---|---|---|
| 0 425 921 | 5/1991 | European Pat. Off. . |
| 0 459 136 | 12/1991 | European Pat. Off. . |
| 0 520 423 | 12/1992 | European Pat. Off. . |

OTHER PUBLICATIONS

J. Tanaka, "Effect of Angiotensin II Receptor Antagonist Drug (TCV–116) in Viral Myocarditis", Japanese Circulation Journal, vol. 57, Suppl. 1, p. 119, item 468, Mar. (1993). Supplement to the Journal of the American College of Cardiology, vol. 21, No. 2, p. 197A (1993).

S. Rezkalla et al., Beneficial Effect of Captopril in Acute Coxsackievirs $B_3$ Murine Myocarditis Circulation, vol. 81, No. 3, Mar. 1990.

A. Masumori, "Lessons from Animal Experiments in Myocarditis", Herz, vol. 17, No. 2, 1992, pp. 107–111.

*Primary Examiner*—Shailendra Kumar
*Attorney, Agent, or Firm*—Foley & Lardner

[57] ABSTRACT

An angiotensin II antagonist compound is administered to mammals with viral disease. This administration ameliorates virus-associated cell injuries, producing therapeutic effects in viral diseases. This compound is also useful for the prevention of such diseases.

14 Claims, No Drawings

TREATMENT FOR VIRAL DISEASES

This application is a division of application Ser. No. 08/200,686, filed Feb. 23, 1994, now U.S. Pat. No. 5,605,919.

INDUSTRIAL FIELD OF UTILIZATION

The present invention relates to pharmaceutical composition for viral diseases which comprises an angiotensin II antagonist compound as an active ingredient.

PRIOR ART

Virus vaccines are chiefly used in the prevention of viral diseases but each vaccine is specific and effective only for the corresponding virus. While there exist many kinds of viruses, vaccines commercially available today are limited in kind. Furthermore, each virus has many mutants and it is often the case that a vaccine is not effective for all strains of the same virus. It is also a very difficult task to develop vaccines with low risks of side effects.

Meanwhile, a variety of antiviral drugs (aciclovir, ganciclovir, Ala-A, etc.) have been developed and clinically in use but they are effective only for very limited types of viral infections and no drug is available that is effective for a variety of viral diseases. Moreover, the administration of such antiviral drugs may entail severe adverse reactions prohibiting clinical application. In recent years, interferons have come to be used in the treatment of some diseases inclusive of viral hepatitis but side effects inclusive of fever have been reported with high frequencies. Moreover, while interferons do actually inhibit the proliferation of viruses, there is no report suggesting that they directly protect the cells from damages. Gamma-globulin is prevalently used in the treatment of viral diseases but clinical responses are not necessarily constant and definite.

PROBLEMS THAT THE INVENTION IS TO SOLVE

Viruses vary a great deal as mentioned above and it is difficult to institute therapies specific to the respective viruses. Therefore, it is an objective of paramount importance to prevent or ameliorate cellular damages in various organs which occur in a variety of viral diseases. It is generally acknowledged that the cell injury in viral diseases includes not only direct damages inflicted by the proliferation of viruses but is associated with various immunologic reactions elicited by infection with viruses. The present invention has for its object to provide a prophylactic/therapeutic regimen for viral diseases which is directed to the prevention and treatment of cell injuries in various organs regardless of the type of virus involved.

SUMMARY OF THE INVENTION

Under the circumstances the inventor of the present invention explored into the domain of prophylactic/therapeutic treatment of viral diseases and found surprisingly that the use of compounds having angiotensin II antagonistic activity results in accomplishment of the above-mentioned object and have brought the present invention into being.

Therefore, the present invention provides a prophylactic/therapeutic composition for viral diseases comprising an angiotensin II antagonist compound as an active ingredient.

DETAILED EXPLANATION OF THE INVENTION

An angiotensin II antagonist compound used in the present invention includes a compound of the following formula (I).

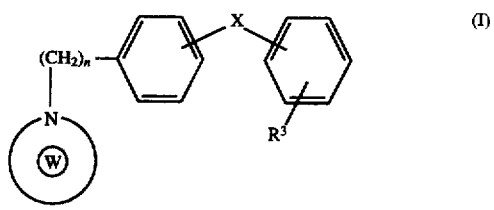

wherein the ring W represents a nitrogen-containing heterocyclic residue which may be substituted; $R^3$ represents a group capable of forming or transformable to an anion; X signifies that the phenylene and phenyl groups are coupled either directly or indirectly through a spacer comprising a chain of not more than 2 atoms; n represents a whole number of 1 or 2, or a salt thereof.

The salt mentioned above is a pharmacologically acceptable salt, thus including salts with inorganic bases, salts with organic bases, salts with inorganic acids, salts with organic acids and salts with basic or acidic amino acids. The preferred salts with inorganic bases are salts with alkali metals such as the sodium, potassium, etc., salts with alkaline earth metals such as calcium, magnesium, etc., aluminum salt and ammonium salt. The preferred salts with organic bases are salts with trimethylamine, triethylamine, pyridine, picoline, ethanolamine, diethanolamine, triethanolamine, dicyclohexylamine, N,N'-dibenzylethylenediamine and so on. The preferred salts with inorganic acids are salts with hydrochloric acid, hydrobromic acid, nitric acid, sulfuric acid, phosphoric acid and so on. The preferred salts with organic acids are salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and so on. The preferred salts with basic amino acids are salts with arginine, lysine, ornithine and so on. The preferred salts with acidic amino acids are salts with aspartic acid, glutamic acid and so on.

Referring to the above formula (I), the group $R^3$ which is capable of forming an anion (a group having a hydrogen atom which can be released as a proton) or transformable to an anion is a 5- through 7-membered (preferably 5- or 6-membered) monocyclic heterocyclic residue containing one or more hetero-atoms of N, S and/or O or a group capable of biotransformation to such a group. Examples are

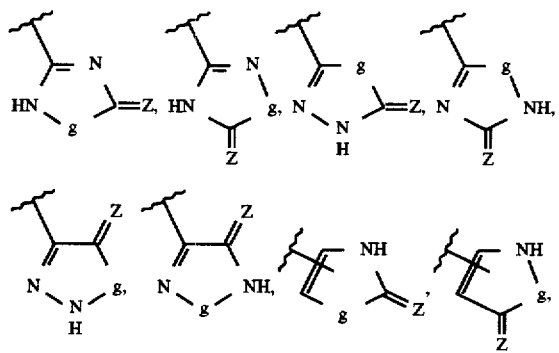

3
-continued

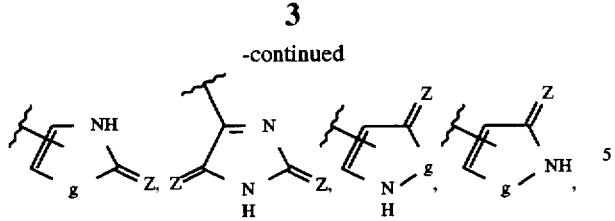

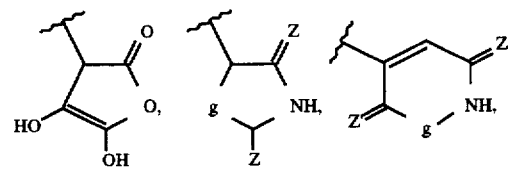

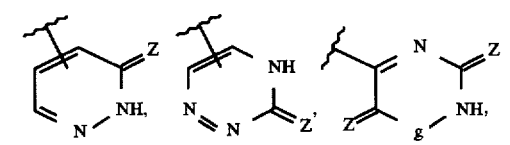

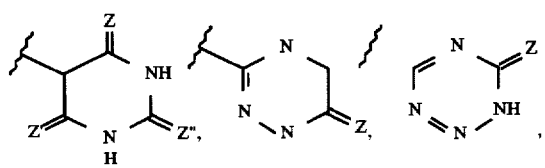

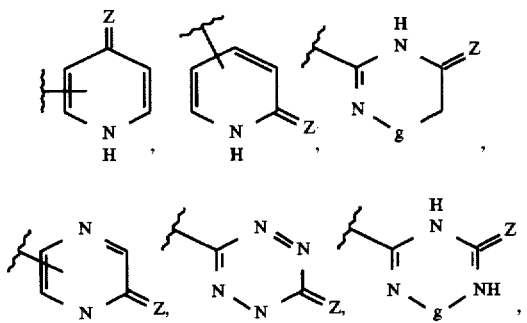

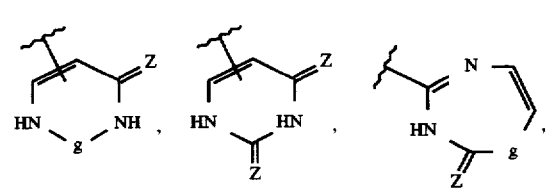

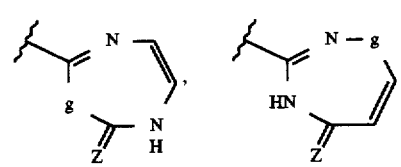

The bond between the group $R^3$ and the phenyl group to which it is attached is not limited to the carbon-carbon bond shown above but may be a bond formed through one of plural nitrogen atoms that exist when g in the above formula is —NH—, for instance.

The following are examples:

4

When $R^3$ is

there may be mentioned

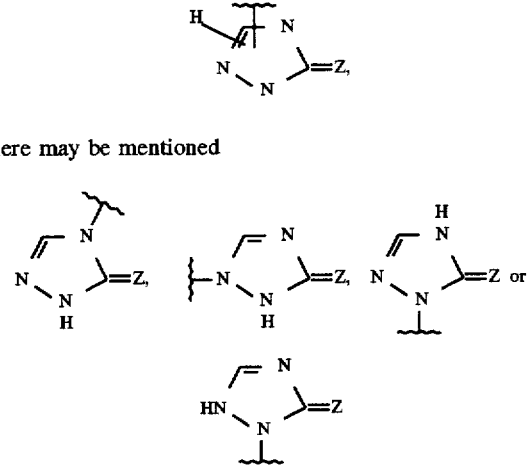

As other examples of $R^3$ which bind through one of nitrogen atoms, there may be mentioned

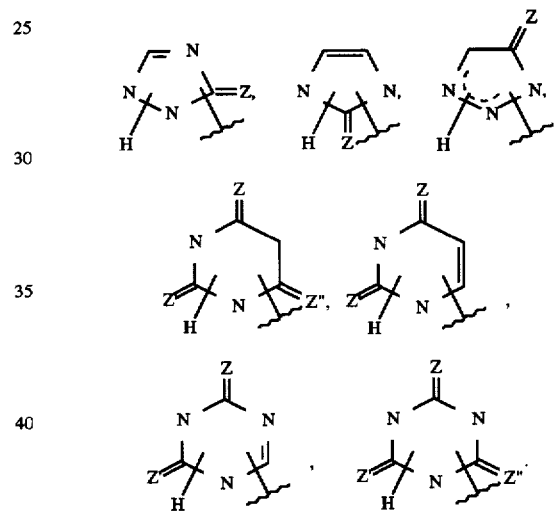

Wherein g is —CH$_2$—, —NR$^5$—, oxygen atom or

wherein >=Z, >=Z' and >=Z" each represents a carbonyl group, a thiocarbonyl group or a sulfur atom which may be oxidized (e.g. S, S(O), S(O$_2$), etc.) and among others there are preferably mentioned carbonyl or thiocarbonyl, more desirably carbonyl; m represents a whole number of 0, 1 or 2; $R^5$ represents a hydrogen atom or a lower alkyl group which may be substituted.

The heterocyclic residue mentioned above is preferably a residue having both a proton-donating group, e.g. —NH or —OH, and a proton-accepting group, e.g. carbonyl, thiocarbonyl or sulfinyl, such as the residue of an oxadiazolone ring, oxadiazolothione ring or thiadiazolone ring, for instance. The heterocyclic residue $R^3$ may also be a group such that a cyclic substituent group is condensed to the heterocycle to form a fused ring structure, although $R^3$ is preferably a 5- or 6-membered ring residue and more desirably a 5-membered ring residue. Moreover, these groups may be protected by lower alkyl groups which may be substituted or acyl groups. Thus, any group that is chemically capable of forming an anion or transformable to an anion under biological or physiological conditions (e.g. by biological transformation such as oxidation, reduction or hydrolysis by physiological enzymes) can be employed.

$R^3$ is preferably a group of the formula

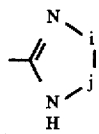

wherein i represents —O— or —S—; j represents >=O, >=S or >=S(O)$_m$; m is as defined hereinbefore. There are preferably mentioned 2,5-dihydro-5-oxo-1,2,4-oxadiazol3-yl, 2,5-dihydro-5-thioxo-1,2,4-oxadiazol-3-yl and 2,5-dihydro-5-oxo-1,2,4-thiadiazol-3-yl. The substituting position of $R^3$ may be ortho, meta or para. Particularly preferred is the ortho-position.

The heterocyclic residue ($R^3$) may exist as tautomers. For example, there are three tautomers a', b' and c' as in

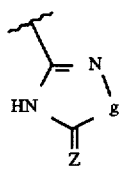

where Z is O and g is O,

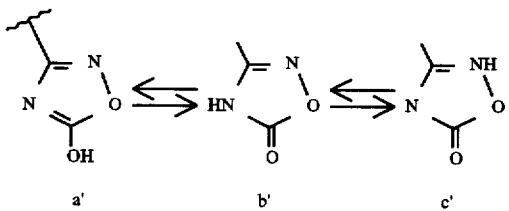

The heterocyclyl group of the formula

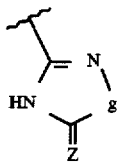

includes all of a', b', and c'.

Furthermore, $R^3$ may be carboxyl, tetrazolyl, trifluoromethanesulfonamido(—NHSO$_2$CF$_3$), phosphate, sulfo, cyano, lower(C$_{1-4}$)alkoxycarbonyl or the like. These groups may be protected by lower alkyl groups which may be substituted or acyl groups, for instance. All that is necessary is that $R^3$ be a group chemically capable of forming or transformable to an anion under biological or physiological conditions (e.g. by biotransformation such as oxidation, reduction or hydrolysis by physiological enzymes).

$R^3$ is preferably a tetrazolyl or carboxyl (more desirably tetrazoyl) group which may be protected by a lower(C$_{1-4}$) alkyl group which may be substituted (e.g. methyl, triphenylmethyl, methoxymethyl, ethoxymethyl, p-methoxybenzyl, p-nitrobenzyl, etc.) or an acyl group (e.g. lower(C$_{2-5}$) alkanoyl, benzoyl, etc.). The substituting position of $R^3$ may be ortho, meta or para. Particularly preferred is the ortho-position.

X signifies that the adjacent phenylene and phenyl groups are coupled either directly or indirectly through a spacer comprising a chain of not more than 2 spacer atoms (preferably directly). This spacer may be any divalent chain whose linear moiety comprises 1 or 2 atoms and may be branched. Thus, lower(C$_{1-4}$) alkylene groups, —CO—, —O—, —S—, —NH—, —CO—NH—, —O—CH$_2$—, —S—CH$_2$—, —CH=CH—, etc. can be mentioned.

Furthermore, n represents a whole number of 1 or 2 (preferably 1).

The structure formed by said $R^3$, X and n

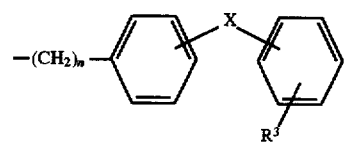

is preferably the following:

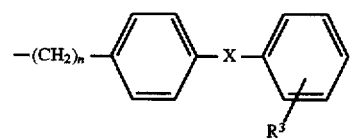

The following is a partial list of the representative nitrogen-containing heterocyclic residues represented by the ring W.

In the following formulas, $R^1$ represents a hydrogen atom or a hydrocarbon residue which may be substituted; Y represents a bond, —O—, —S(O)$_m$- (where m is 0, 1 or 2) or —N(R$^4$)— (where $R^4$ is a hydrogen atom or an alkyl group which may be substituted). Preferably, $R^1$ is a lower (C$_{1-5}$) alkyl (more preferably a lower(C$_{1-4}$) alkyl) group which may be substituted by hydroxy, amino, halogen or lower(C$_{1-4}$) alkoxy and Y is a bond, —O—, —S— or —N(R$^4$)— (where $R^4$ is hydrogen or lower(C$_{1-4}$) alkyl).

Regarding the residue of formula (III)

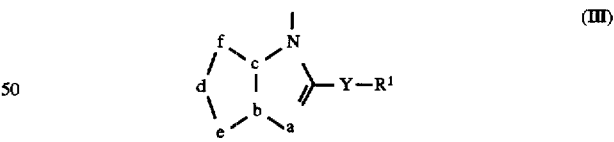

(III)

wherein a and e constituting the heterocyclic residue independently represent 1 or 2 carbon or hetero atoms which may be substituted, d and f independently represent one carbon or hetero atom which may be substituted, and b and c independently represent one carbon or nitrogen atom which may be substituted, the following residues can be mentioned.

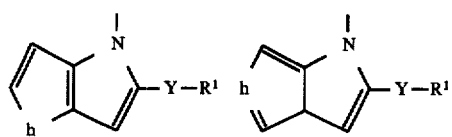

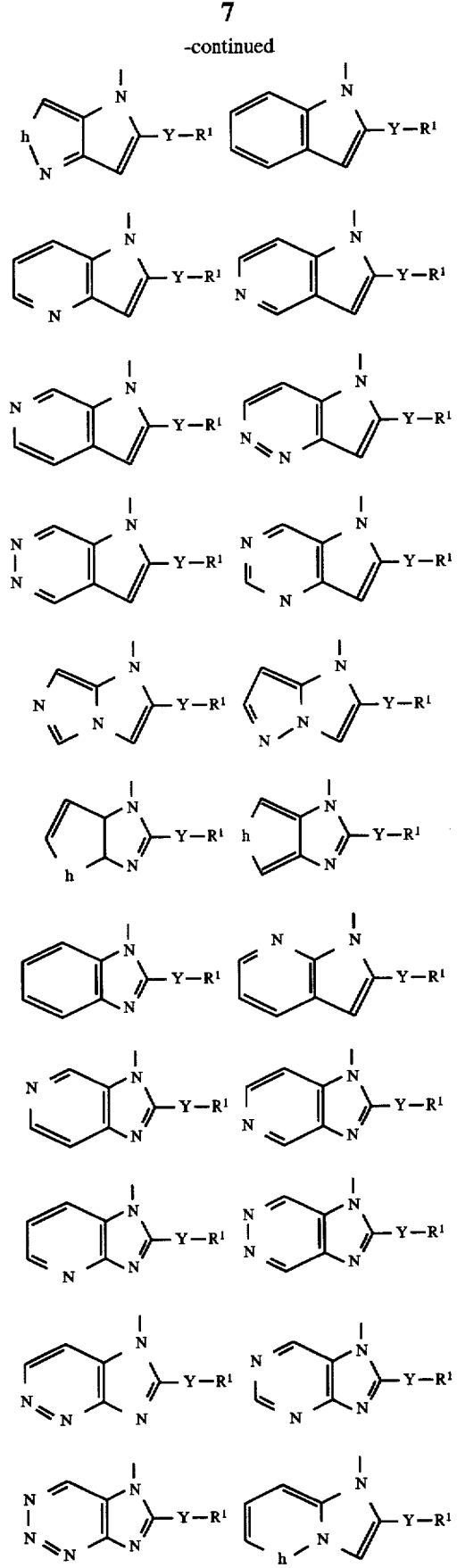
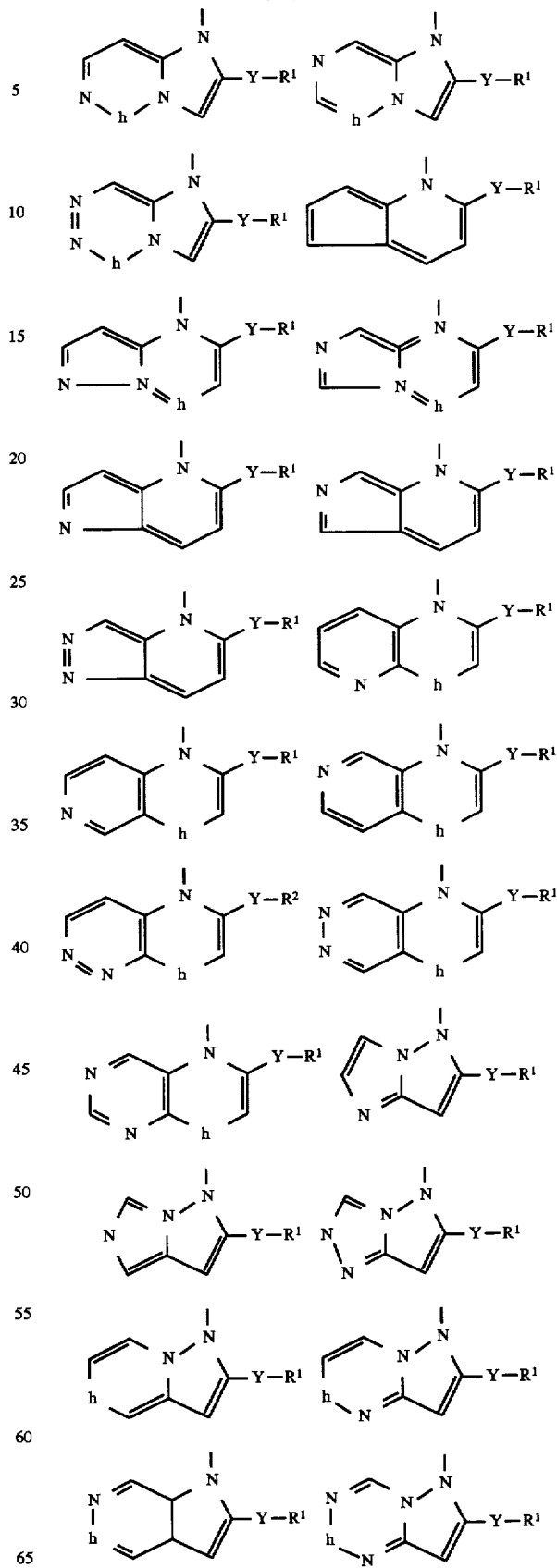

-continued

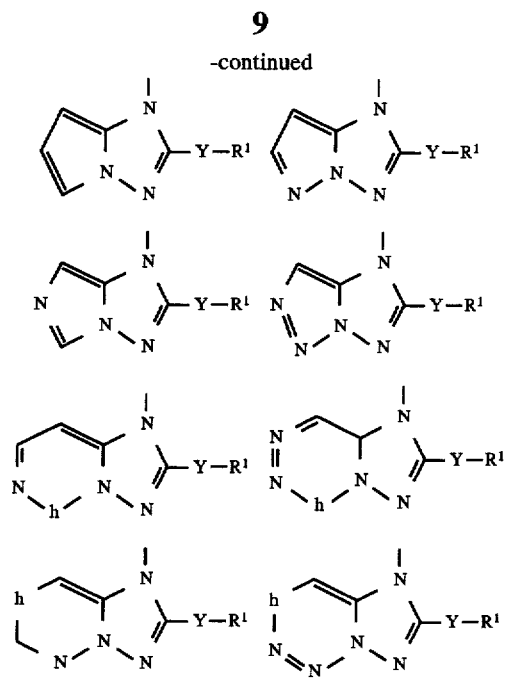

wherein h represents —CH$_2$—, >=O, >=S, >S—(O)$_m$, —N(R$^4$)— or —O—; m represents 0, 1 or 2; R$^4$ represents hydrogen or an alkyl group which may be substituted (preferably hydrogen or lower(C$_{1-4}$) alkyl).

Furthermore, as the residue of formula (IV):

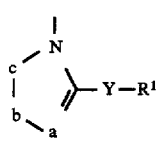
(IV)

(wherein a and b constituting the heterocyclic residue independently represent one or two carbon or hetero atoms which may be substituted; c represents one carbon or hetero atom which may be substituted), there can be mentioned the following:

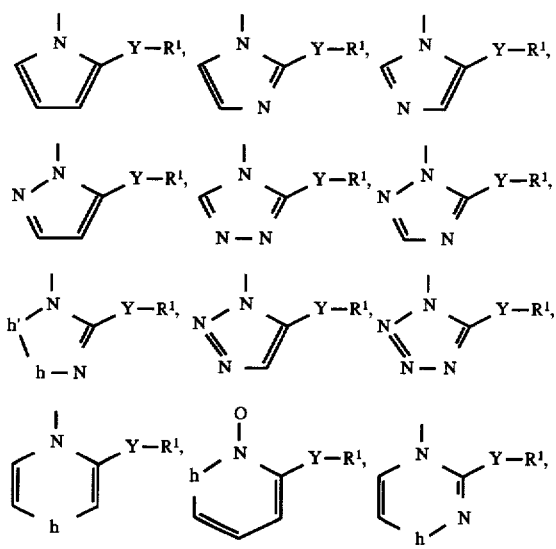

-continued

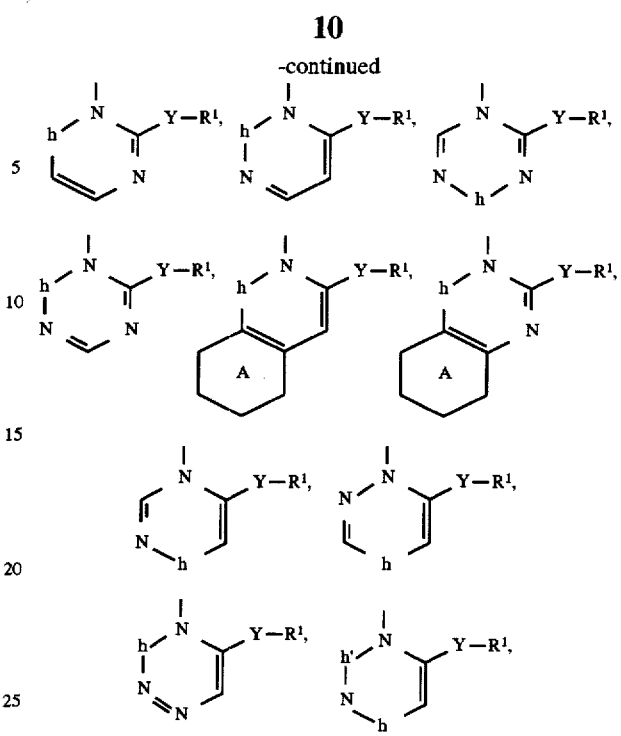

wherein A represents an aromatic hydrocarbon residue optionally containing a hetero atom or a heterocyclic residue, which may be substituted (preferably an aromatic hydrocarbon residue such as phenyl); h and h' each represents —CH$_2$—, >=O, >=S, >S—(O)$_m$, —N(R$^4$)— or —O—; m and R$^4$ are as defined hereinbefore. It should be understood that these structures are not exclusive but are merely illustrative.

The heterocyclic group of formula (III) may be substituted by a group represented by R$^2$ (e.g. a group capable of forming or transformable to an anion) in addition to the group Y—R$^1$. The preferred substituting position of R$^2$ is the position of the atom indicated by f in the formula (III).

The group R$^2$ which is capable of forming or transformable to an anion includes, among others, carboxyl which may be esterified or amidated, tetrazolyl, trifluoromethanesulfonamido(-NHSO$_2$CF$_3$), phosphate, sulfonate, etc. and these groups may be respectively protected by a lower alkyl group which may be substituted or an acyl group. Thus, it may be any group chemically capable of forming or transformable to an anion under biological or physiological conditions (e.g. by biotransformation such as oxidation, reduction or hydrolysis by physiological enzymes).

The carboxyl group which may be esterified or amidated, as represented by R$^2$, includes, among others, groups of the formula —CO—D, wherein D represents a hydroxyl group, an amino group which may be substituted (e.g. amino, N-lower(C$_{1-4}$)alkylamino, N,N-dilower(C$_{1-4}$)alkylamino, etc.) or an alkoxy group which may be substituted {lower (C$_{1-6}$) alkoxy groups whose alkyl moieties may be substituted by hydroxyl, amino which may be substituted (e.g. amino, dimethylamino, diethylamino, piperidino, morpholino, etc.), halogen, lower(C$_{1-6}$) alkoxy, lower(C$_{1-6}$) alkylthio or dioxolenyl which may be substituted (e.g. 5-methyl-2-oxo-1,3-dioxolen-4-yl) or a group of the formula —O—CH(R$^6$)—OCOR$^5$, wherein R$^6$ represents hydrogen, a straight-chain or branched lower(C$_{1-6}$) alkyl group (e.g.methyl, ethyl, n-propyl, isoproyl, n-butyl, isobutyl, t-butyl, n-pentyl, isopentyl, neopentyl, etc.), a straight-chain or branched lower($C_{2-4}$) alkenyl group or a $C_{3-8}$ cycloalkyl group (e.g. cyclopentyl, cyclohexyl, cycloheptyl, etc.); $R^5$ is a straight-chain or branched lower($C_{1-6}$) alkyl group (e.g. methyl, ethyl, n-propyl, isopropyl, n-butyl, isobutyl, sec-butyl, t-butyl, n-pentyl, isopentyl, neopentyl, etc.), a straight-chain or branched lower($C_{2-6}$) alkenyl group, a lower($C_{1-3}$) alkyl group substituted by $C_{3-8}$ cycloalkyl (e.g. cyclopentyl, cyclohexyl, cycloheptyl, etc.) or aryl (e.g. phenyl) which may be substituted (e.g. benzyl, p-chlorobenzyl, phenethyl, cyclopentylmethyl, cyclohexylmethyl, etc.), a lower($C_{2-3}$) alkenyl group which may be substituted by $C_{3-8}$ cycloalkyl or aryl (e.g. phenyl) which may be substituted (e.g. those containing such alkenyl groups as vinyl, propenyl, allyl, isopropenyl, etc.; an example is cinnamyl), an aryl group, e.g. phenyl, which may be substituted (e.g. phenyl, p-tolyl, naphthyl, etc.), a straight-chain or branched lower($C_{1-6}$) alkoxy group (e.g. methoxy, ethoxy, n-propoxy, isopropoxy, n-butoxy, isobutoxy, sec-butoxy, t-butoxy, n-pentyloxy, isopentyloxy, neopentyloxy, etc.), a straight-chain or branched lower($C_{2-8}$)alkenyloxy group (e.g. allyloxy, isobutenyloxy, etc.), a $C_{3-8}$ cycloalkyloxy group (e.g cyclopentyloxy, cyclohexyloxy, cycloheptyloxy, etc.), a $C_{1-3}$ lower alkoxy group which may be substituted by $C_{3-8}$ cycloalkyl (e.g. cyclopentyl, cyclohexyl, cycloheptyl, etc.) or aryl, e.g. phenyl, which may be substituted (e.g. those having such alkoxy moieties as methoxy, ethoxy, n-propoxy, isopropoxy, etc.; e.g. benzyloxy, phenethyloxy, cyclopentylmethoxy, cyclohexylmethoxy, etc.), a lower($C_{2-3}$)alkenyloxy group substituted by $C_{3-8}$ cycloalkyl (e.g. cyclopentyl, cyclohexyl, cycloheptyl, etc.) or aryl, e.g. phenyl, which may be substituted (e.g. those groups which have such alkenyloxy moieties as vinyloxy, propenyloxy, allyloxy, isopropenyloxy, etc.; e.g. cinnamyloxy) or an aryloxy group such as phenyloxy which may be substituted (e.g. phenoxy, p-nitrophenoxy, naphthoxy, etc.)}.

The substituent group $R^2$ may be a tetrazoyl, trifluoromethanesulfonamido, phosphate or sulfonate group protected by a group capable of forming or transformable to an anion [e.g. alkyl (e.g. lower($C_{1-4}$) alkyl) or acyl (e.g. lower($C_{2-5}$) alkanoyl, benzoyl which may be substituted]. The substitutent group $R^2$ thus includes —COOH and its salt, —COOMe, —COOEt, —COOt-Bu, —COOPr, pivaloyloxymethoxycarbonyl, 1-(cyclohexyloxycarbonyloxy)ethoxycarbonyl, 5-methyl-2-oxo-1,3-dioxolen-4-ylmethoxycarbonyl, acetoxymethoxycarbonyl, propionyloxymethoxycarbonyl, n-butyroxymethoxycarbonyl, isobutyroxymethoxycarbonyl, 1-(ethoxycarbonyloxy)ethoxycarbonyl, 1-(acetoxy)ethoxycarbonyl, 1-(isobutyroxy)ethoxycarbonyl, cyclohexyl-carbonyloxymethoxycarbonyl, benzoyloxymethoxycarbonyl, cinnamyloxycarbonyl, cyclopentylcarbonyloxymethylcarbonyl and so on. Moreover, $R^2$ may be any group that is chemically capable of forming an anion or transformable to an anion (e.g. COO⁻ or a derivative thereof) under biological or physiological conditions (e.g. biotransformation such as oxidation, reduction or hydrolysis by physiological enzymes). $R^2$ may also be a carboxyl group or a prodrug form thereof. $R^2$ may also be a group which is biologically or chemically transformed into an anion in the living body, for instance.

The preferred group $R^2$ is a group of the formula —CO—D, wherein D represents a hydroxyl group or a lower($C_{1-4}$) alkoxy group the alkyl moiety of which may be substituted by hydroxy, amino, halogen, lower($C_{2-6}$)alkanoyloxy (e.g. acetoxy, pivaloyloxy, etc.), lower($C_{1-6}$) alkoxycarbonyloxy (e.g. methoxycarbonyloxy, ethoxycarbonyloxy, cyclohexyloxycarbonyloxy, etc.) or lower($C_{1-4}$) alkoxy.

The heterocyclic residue of formula (III) may have substituents in addition to the groups represented by Y—$R^1$ and $R^2$, thus including halogen (e.g. F, Cl, Br, etc.), cyano, nitro, lower($C_{1-4}$) alkyl, lower($C_{1-4}$) alkoxy, amino which may be substituted (e.g. amino, N-(lower)($C_{1-4}$)alkylamino (e.g. methylamino etc.), N,N-di(lower)($C_{1-4}$)alkylamino (e.g. dimethylamino etc.), N-arylamino (e.g. phenylamino etc.), alicyclic amino (e.g. morpholino, piperidino, piperazino, N-phenylpiperazino etc.), a group of the formula —CO—D', wherein D' represents a hydroxyl group or a lower($C_{1-4}$) alkoxy group the alkyl moiety of which may be substituted by hydroxy, lower($C_{1-4}$) alkoxy, lower($C_{2-6}$)alkanoyloxy (e.g. acetoxy, pivaloyloxy, etc.) or lower($C_{1-6}$) alkoxycarbonyloxy (e.g. methoxycarbonyloxy, ethoxycarbonyloxy, cyclohexyloxycarbonyloxy, etc.), a tetrazolyl group which may be protected by lower($C_{1-4}$) alkyl or acyl (e.g. lower($C_{2-5}$) alkanoyl, benzoyl which may be substituted, etc.), trifluoromethanesulfonamido, a phosphoric acid group or a sulfonic acid group. The preferred substitutes are lower($C_{1-4}$) alkyl and halogen. These substituents may be situated in 1 or 2 optional substitutable positions of the cyclic structure.

The fused heterocycle of formula (III) preferably has the formula

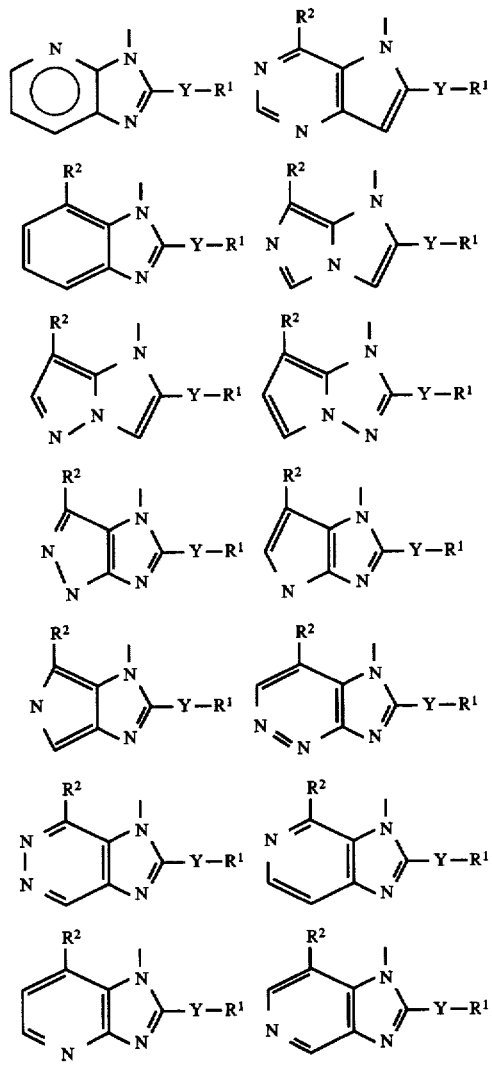

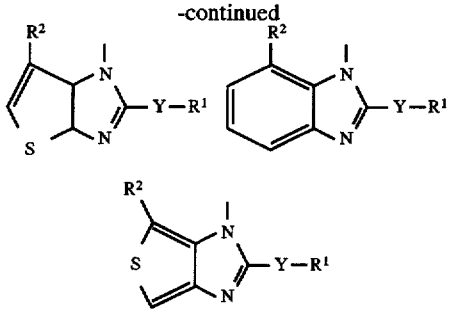

wherein Y—R¹ and R² are as defined hereinbefore. Preferred are compounds having a benzimidazole, thienoimidazole or imidazopyridine structure (benzimidazole and thienoimidazole, in particular).

The above heterocyclic residue of formula (IV) may have further substituents in addition to the group represented by Y—R¹, such as halogen (e.g. F, Cl, Br, etc.), cyano, nitro, lower($C_{1-4}$) alkyl which may be substituted, lower($C_{1-4}$) alkoxy, amino which may be substituted (e.g. amino, N-lower($C_{1-4}$)alkylamino (e.g. methylamino etc.), N,N-di (lower)($C_{1-4}$)alkylamino (e.g. dimethylamino etc.), N-arylamino (e.g. phenylamino etc.), alicyclic amino (e.g. morpholino, piperidino, piperazino, N-phenylpiperazine etc.), a group of the formula —CO—D' [wherein D' represents a hydroxyl group or a lower($C_{1-4}$) alkoxy group the alkyl moiety of which may be substituted by hydroxy, lower($C_{1-4}$) alkoxy, lower($C_{2-6}$)alkanoyloxy (e.g. acetoxy, pivaloyloxy, etc.) or lower($C_{1-6}$)alkoxycarbonyloxy (e.g. methoxycarbonyloxy, ethoxycarbonyloxy, cyclohexylcarbonyloxy, etc.)] or a tetrazolyl group which may be protected by lower($C_{1-4}$) alkyl or acyl (e.g. lower ($C_{2-5}$)alkanoyl, benzoyl which may be substituted, etc.) trifluoromethanesulfonamido, a phosphoric acid group or a sulfonic acid group. The preferred are lower($C_{1-4}$) alkyl groups which may be substituted and halogen atoms. These substituents may be concurrently situated in one or two optional substitutable positions of the cyclic structure. The substituent for said lower($C_{1-4}$) alkyl which may be substituted includes hydroxy, carboxy and halogen.

The ring W includes a benzimidazole ring of the formula:

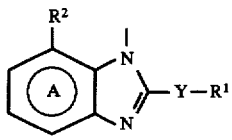

wherein the ring A represents a benzene ring optionally having one or more substituent groups in addition to a group represented by R²; R¹ represents a hydrogen atom or a hydrocarbon residue which may be substituted; R² represents a carboxyl group which may be esterified; Y represents a bond, —O—, —S(O)$_m$- (where m is 0, 1 or 2) or —N(R⁴)— (where R⁴ is hydrogen or an alkyl group which may be substituted).

The compound of formula (I) includes compounds of the formula

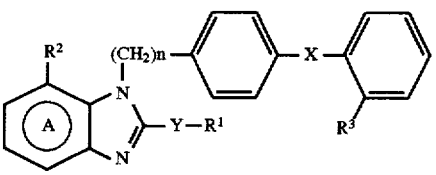

wherein the ring A represents a benzene ring optionally having substituents in addition to the group R²; R¹ represents a hydrogen atom or a hydrocarbon residue which may be substituted; R³ represents a group capable of forming or transformable to an anion; X signifies that the phenylene group and phenyl group are joined to each other either directly or through a spacer comprising a chain of not more than 2 spacer atoms; R² represents a carboxyl group which may be esterified; Y represents a bond, —O—, —S(O)$_m$- (where m represents 0, 1 or 2) or —N(R⁴)— (where R⁴ represents a hydrogen atom or an alkyl group which may be substituted); n represents a whole number of 1 or 2, and salts thereof and more specifically the benzimidazole-7-carboxylic acid compounds and their derivatives described in Japanese published unexamined patent application (Kokai Tokkyo Koho) No. 9373/1992, and 364171/1992, and EP 520423. Particularly preferred are compounds of formula (I') which corresponds to the above formula (I) wherein R¹ represents a lower($C_{1-5}$) alkyl group (preferably a lower($C_{1-4}$) alkyl group) which may be substituted by hydroxy, amino, halogen or lower($C_{1-4}$) alkoxy; R² represents a group of the formula —CO—D, wherein D represents a hydroxyl group or a lower($C_{1-4}$) alkoxy group the alkyl moiety of which may be substituted by hydroxy, amino, halogen, lower($C_{2-6}$) alkanoyloxy (e.g. acetoxy, pivaloyloxy, etc.), lower($C_{1-6}$) alkoxycarbonyloxy (e.g. methoxycarbonyloxy, ethoxycarbonyloxy, cyclohexyloxycarbonyloxy, etc.) or lower($C_{1-4}$) alkoxy J; the ring A represents a benzene ring which may be substituted, in addition to group R², by halogen (e.g. F, Cl, Br, etc.), lower($C_{1-4}$) alkyl, lower($C_{1-4}$) alkoxy, nitro, a group of the formula —CO—D', wherein D' represents a hydroxyl group or a lower($C_{1-4}$) alkoxy group the alkyl moiety of which may be substituted by hydroxy, lower($C_{1-4}$) alkoxy, lower($C_{2-6}$)alkanoyloxy (e.g. acetoxy, pivaloyloxy, etc.) or lower($C_{1-6}$)alkoxycarbonyloxy (e.g. methoxycarbonyloxy, ethoxycarbonyloxy, cyclohexyloxycarbonyloxy, etc.), or an amino group which may be substituted by lower($C_{1-4}$) alkyl (preferably a benzene ring substituted by lower($C_{1-4}$) alkyl or halogen, and more preferably a benzene ring having no substituent other than a group of the formula R²); Y represents —N(R⁴)— [wherein R⁴ represents hydrogen or lower($C_{1-4}$) alkyl]; R³ represents a tetrazolyl or carboxyl group (preferably tetrazolyl) which may be protected by a lower($C_{1-4}$) alkyl group which may also be substituted (e.g. methyl, triphenylmethyl, methoxymethyl, ethoxymethyl, p-methoxybenzyl, p-nitrobenzyl, etc.) or an acyl group (e.g. lower($C_{2-5}$)alkanoyl, benzoyl, etc.); n represents 1; X represents a bond.

Angiotensin II antagonist compound used in the present invention include compounds disclosed in the specifications of U.S. Pat. No. 5,183,899, EP0425921A1, EP0430300A2, EP0434038A1, EP0442473A1,
EP0443568A1, EP0445811A2, EP0459136A1, EP0483683A2, EP0520423A2, EP Application No. 93.114754.0 and EP application No. 93.120135.4.

As the preferred compounds for use as the active ingredient in the present invention may be mentioned the compounds described in the examples of Japanese published unexamined patent application (Kokai Tokkyo Koho) No. 364171/1992 or EP0459135A1 and EP 520423A2.

As compounds of formula (I) may be mentioned the compounds disclosed inter alia in Japanese published unexamined patent application (Kokai Tokkyo Koho) No. 9373/1992, Japanese published unexamined patent application (Kokai Tokkyo Koho) No. 364171/1992 and EP 520423 and these compounds can be produced by the processes described in the same patent literature.

The compound of formula (I) which is used as the angiotensin II antagonist compound in the present invention is low in toxicity and of value as a prophylactic/therapeutic agent for viral diseases in animals, particularly mammalian animals (such as man, dog, rabbit, mouse, rat, etc.).

The viral disease addressed by the present invention includes those diseases which are caused or induced by pathogenic viruses belonging to either the category of DNA viruses or the category of RNA viruses. Examples of such viruses are presented below.

DNA viruses: Poxviruses, herpesviruses, adenoviruses, parvoviruses

RNA viruses: Revoviruses, togaviruses, coronaviruses, rhabdoviruses, paramyxoviruses, orthomyxoviruses, bunyaviruses, arena-viruses, retroviruses, picornaviruses, caliciviruses The specific viral diseases include viral hepatitis (A, B, C, E), influenza, viral pneumonia, viral bronchitis, herpetic infections (simplex virus, EB virus (infectious mononucleosis), herpes zoster), poliomyelitis, AIDS (HIV infection), adult T-cell leukemia (ATL), papilloma, measles, rubella, exanthema subitum, erythema infectiosum, viral encephalitis, viral myelitis, cytomegalovirus infection, mumps, varicella, rabies, viral enteritis, viral myocarditis, viral pericarditis and so on.

Among others, the present invention is preferably applicable for treatment or prevention of diseases which are caused or induced by RNA viruses or hepatitis viruses. There are particularly mentioned orthomyxoviruses or picornaviruses as RNA viruses. In addition, there are particularly mentioned viral hepatitis (A, B, C, E), influenza, viral encephalitis, viral enteritis, viral myocarditis or viral pericarditis among viral diseased described above.

The compound of formula (I) or a salt thereof can be administered orally, parenterally, by inhalation, intrarectally or topically. It can be used in the form of a pharmaceutical composition or preparation (e.g. powders, granules, tablets, pills, capsules, injections, syrups, emulsions, elixers, suspensions, solutions, etc.) containing at least one species of the compound of the invention in combination with a pharmaceutically acceptable carrier (such as adjuvants, excipients, ointment bases and/or diluents).

The composition or preparation for medical use can be manufactured by the conventional procedures. As used in this specification, the term 'parenteral' or 'parenterally' refers to any of the subcutaneous, intravenous, intramuscular, intraperitoneal, drip and other routes or methods of administration. Injectable preparations, for example sterile aqueous or oily suspensions for injection can be manufactured by the procedure well established in the field using an appropriate dispersant or wetting agent and a suspending agent. The sterile injectable preparations may also be sterile solutions or suspensions in water, a nontoxic diluent, solvent or vehicle acceptable for purposes of injection. As examples of said vehicle or solvent may be mentioned water, Ringer's solution, isotonic saline and the like. Moreover, sterile nonvolatile oils can be used as the solvent or suspension vehicle. For such purposes, virtually any type of nonvolatile oil or fatty acid can be used. Thus, natural, synthetic and semisynthetic fatty oils or fatty acids and natural, synthetic and semisynthetic mono-, di- or triglycerides can be mentioned.

Suppositories for rectal administration can be manufactured using the active ingredient and a suitable non-irritating base such as cocoa butter, polyethylene glycol and other substances which are solid at room temperature but liquid at the rectal temperature and, as such, would melt in the rectum to release the active ingredient.

The solid dosage form for oral administration includes the above-mentioned powders, granules, tablets, pills, capsules and so on. To manufacture such a solid dosage form, the active ingredient compound can be mixed with at least one additive such as sucrose, lactose, cellulose and its derivatives, mannitol, maltitol, dextran, starch, agar, aliginates, chitins, chitosans, pectin, gum tragacanth, gum arabic, gelatin, collagen, casein, albumin, synthetic or semisynthetic polymers and glycerides. Such dosage forms may, as usual, contain further additives, e.g. inert diluents, lubricants such as magnesium stearate, preservatives such as parabens, sorbic acid, etc., antioxidants such as ascorbic acid, α-tocopherol, cysteine, etc., disintegrators, binders, thickeners, buffers, sweeteners, flavorants, perfumes and so on. Tablets and pills may be enteric-coated. The liquid for oral administration includes medicinally acceptable emulsions, syrups, elixirs, suspensions, solutions, etc. which may contain any inert diluent that is routinely used in the field of art, such as water.

The dosage for any specific patient or individual is determined according to such parameters as age, body weight, general physical condition, sex, diet, drip time, therapeutic regimen, excretion rate, combination of plural drugs, current stage of disease to be managed and so on.

The compound of general formula (I) or a salt thereof is low in toxicity and can be used safely. The daily dose varies with the patient's condition and body weight, species of compound, administration route, etc. but for administration as a therapeutic drug for viral disease in an adult human, it is preferable that a daily oral dose of 0.5~20 mg or a daily intravenous dose of 0.5~20 mg be administered in a single dose or in 2 or 3 divided doses.

Effect of the Invention

Administration of an angiotensin II antagonist compound in accordance with the present invention ameliorates virus-associated cell injuries, producing therapeutic effects in viral diseases. It is also useful for the prevention of such diseases.

The following test example is intended to demonstrate the biological activity of the angiotensin II antagonist compound and salt.

Test Example

Effect of angiotensin II antagonist compound in viral myocarditis

Compound 1: 1-(Cyclohexyloxycarbonyloxy)ethyl 2-ethoxy-1-[[2'-(1H-tetrazol-5-yl)biphenyl-4-yl]methyl]-1H-benzimidazole-7-carboxylate Method Four-week-old DBA/2 mice were divided into 3 groups (n per group=21) and intraperitoneally inoculated with 10 pfu of encephalomyocarditis (EMC) virus. Starting 2 days after inoculation, control 5% gum arabic solution (vehicle) (Group A), Compound 1, 0.3 mg/kg, (Group A) and Compound 1, 3 mg/kg, (Group C) were respectively administered daily until day 14. The survival rates in the respective groups on day 14 were compared by the method of Kaplan-Mayer. In survivals, body weight (BW), heart weight (HW) and heart/body weight ratio (HW/BW) were determined and the histopathological findings of the heart were scored for each of the three parameters of myocardial cell necrosis, cellular infiltration and calcification on the grading scale of 1 (<25%), 2 (25%≦, <50%), 3 (50%≦, <75%) and 4 (75%≦). The above animal model of dilated cardiomyopathy is described in Circulation, 65:1230–1235, 1982 or Circulation, 66:355–360, 1982.

The blood angiotensin II level was determined by radio-immunoassay. Intergroup comparison was made by ANOVA test.

Results

The survival rates on day 14 were 47.6% in Group A, 47.6% in Group B and 57.1% in Group C. No significant difference was found.

The BW, HW and HW/BW data in survivals were as follows.

| Group | BW (g) | HW (mg) | HW/BW (× $10^3$) |
|---|---|---|---|
| A (n = 10) | 14.7 ± 2.5 | 133 ± 33 | 9.69 ± 4.34 |
| B (n = 10) | 14.2 ± 2.1 | 139 ± 28 | 10.14 ± 3.30 |
| C (n = 12) | 14.6 ± 2.2 | 106 ± 24* | 7.42 ± 1.99 |

*p < 0.05 vs Group A

Pathological findings were as follows.

| Group | Myocardial cell necrosis | Cellular infiltration | Calcification |
|---|---|---|---|
| A (n = 10) | 2.3 ± 1.2 | 2.6 ± 1.3 | 2.1 ± 1.1 |
| B (n = 10) | 1.6 ± 0.5 | 2.3 ± 0.7 | 1.6 ± 0.5 |
| C (n = 12) | 1.1 ± 0.3* | 1.4 ± 0.7* | 1.1 ± 0.3* |

*p < 0.05 vs Group A

Whereas the mean angiotensin II level in noninfected mice (n=5) was 32 pg/ml, that in infected mice (n=6) was elevated to 73 pg/ml.

The above results indicate that, in viral myocarditis, the angiotensin II-receptor antagonist alleviates myocardial damage and suppresses cardiac enlargement following the acute stage.

EXAMPLES

The following examples are intended to describe the invention in further detail and should by no means be construed as defining the scope of the invention.

Formulation Examples

Prophylactic/therapeutic dosage forms for viral diseases, each containing the angiotensin II antagonist compound of the invention as an active ingredient, can be manufactured according to the following exemplary formulations.

| 1. Capsules | |
|---|---|
| (1) 2-Ethoxy-1-[[2'-(1H-tetrazol-5-yl)biphenyl-4-yl]methyl]benzimidazole-7-carboxylic acid | 10 mg |
| (2) Lactose | 90 mg |
| (3) Microcrystalline cellulose | 70 mg |
| (4) Magnesium stearate | 10 mg |
| per capsule | 180 mg |

(1), (2), (3) and one-half of (4) are blended and granulated. To the granulation is added the remainder of (4) and the whole composition is sealed into gelatin capsule shells.

| 2. Tablets | |
|---|---|
| (1) 2-Ethoxy-1-[[2'-(1H-tetrazol-5-yl)biphenyl-4-yl]methyl]benzimidazole-7-carboxylic acid | 10 mg |
| (2) Lactose | 35 mg |
| (3) Corn starch | 150 mg |
| (4) Microcrystalline cellulose | 30 mg |
| (5) Magnesium stearate | 5 mg |
| per tablet | 230 mg |

(1), (2), (3), ⅔ of (4) and ½ of (5) are blended and granulated. To the granulation are added the remainders of (4) and (5) and the whole composition is compression-molded to provide tablets.

| 3. Injection | |
|---|---|
| (1) Disodium 2-methylthio-1-[[2'-(1H-tetrazol-5-yl)biphenyl-4-yl]methyl]benzimidazole-7-carboxylate | 10 mg |
| (2) Inositol | 100 mg |
| (3) Benzyl alcohol | 20 mg |
| per ampule | 130 mg |

(1), (2) and (3) are dissolved in sufficient distilled water for injection to make 2 ml and this solution is sealed into ampules. The whole procedure is carried out under sterile conditions.

| 4. Capsules | |
|---|---|
| (1) 1-(Cyclohexyloxycarbonloxy)ethyl 2-ethoxy-1-[[2'-(1H-tetrazol-5-yl)biphenyl-4-yl]methyl]benzimidazole-7-carboxylate | 10 mg |
| (2) Lactose | 90 mg |
| (3) Microcrystalline cellulose | 70 mg |
| (4) Magnesium stearate | 10 mg |
| per capsule | 180 mg |

(1), (2), (3) and ½ of (4) are blended and granulated. To the granulation is added the remainder of (4) and the whole composition is sealed into gelatin capsule shells.

| 5. Tablets | |
|---|---|
| (1) 1-(Cyclohexyloxycarbonloxy)ethyl 2-ethoxy-1-[[2'-(1H-tetrazol-5-yl)biphenyl-4-yl]methyl]benzimidazole-7-carboxylate | 10 mg |
| (2) Lactose | 35 mg |
| (3) Corn starch | 150 mg |
| (4) Microcrystalline cellulose | 30 mg |
| (5) Magnesium stearate | 5 mg |
| per tablet | 230 mg |

(1), (2), (3), ⅔ of (4) and ½ of (5) are blended and granulated. To the granulation are added the remainders of (4) and (5) and the whole composition is compression-molded into tablets.

|  | 6. Injection |  |
| --- | --- | --- |
| (1) | Disodium 2-ethoxy-1-[[2'-(1H-tetrazol-5-yl)biphenyl-4-yl]methyl]benzimidazole-7-carboxylate | 10 mg |
| (2) | Inositol | 100 mg |
| (3) | Benzyl alcohol | 20 mg |
|  | per ampule | 130 mg |

(1), (2) and (3) are dissolved in sufficient distilled water for injection to make 2 ml and the solution is sealed into ampules. The whole process is carried out under sterile conditions.

What is claimed is:

1. A method for treating diseases caused by virus-associated cell injury in an animal, which comprises administering to said animal an effective amount of an angiotensin II antagonist compound as an active ingredient and a pharmaceutically acceptable carrier, wherein said angiotensin II antagonist compound is a compound of the formula:

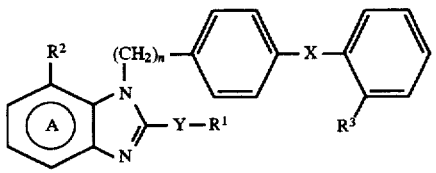

wherein the ring A represents a benzene ring optionally having at least one substituent in addition to $R^2$; $R^1$ represents a hydrogen atom or a hydrocarbon residue which may be substituted; $R^3$ represents a group capable of forming or transformable to an anion; X signifies that the phenylene group and phenyl group are joined to each other either directly or through a spacer comprising a chain of not more than 2 spacer atoms; $R^2$ represents a carboxyl group which may be esterified; Y represents a bond, —O—, —S(O)$_m$— where m represents 0, 1 or 2, or —N($R^4$)— where $R^4$ represents a hydrogen atom or an alkyl group which may be substituted; and n represents a whole number of 1 or 2.

2. The method according to claim 1, wherein $R^2$ represents a group of the formula —CO—D, where D is a hydroxyl group or a lower ($C_{1-4}$), alkoxy group whose alkyl moiety may be substituted by hydroxy, amino, halogen, lower ($C_{2-7}$) alkanoyloxy, lower ($C_{4-9}$) cycloalkanoyloxy, lower ($C_{1-6}$) alkoxycarbonyloxy, lower ($C_{3-8}$) cycloalkoxycarbonyloxy, lower ($C_{1-4}$) alkoxy or lower ($C_{3-8}$) cycloalkoxy.

3. The method according to claim 1, wherein $R^3$ represents a monocyclic heterocyclic residue which may be substituted.

4. The method according to claim 1, wherein $R^3$ represents

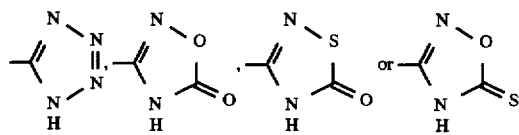

5. The method according to claim 1, wherein the compound of formula (I) is (±) -1-(cyclohexyloxycarbonyloxy) ethyl 2-ethoxy1-[[2'-(1H-tetrazol-5-yl)biphenyl-4-yl] methyl]-1H-benzimidazole-7-carboxylate.

6. The method according to claim 1, wherein the compound of formula (I) is 2-ethoxy-1-[[2'-(1H-tetrazol-5-yl) biphenyl-4-yl]methyl]benzimidazole-7-carboxylic acid.

7. The method according to claim 1, wherein the compound of formula (I) is pivaloyloxymethyl 2-ethoxy-1-[[2'-(1H-tetrazol-5-yl)biphenyl-4-yl]methyl]benzimidazole-7-carboxylate.

8. The method according to claim 1, wherein the compound of formula (I) is 2-ethoxy-1-[[2'-(4,5-dihydro-5-oxo-1,2,4oxadiazol-3-yl) biphenyl-4-yl]methyl]benzimidazole-7-carboxylic acid.

9. The method according to claim 1, wherein the viral diseases are diseases caused or induced by RNA viruses or hepatitis viruses.

10. The method according to claim 9, wherein the RNA viruses are orthomyxoviruses or picornaviruses.

11. The method according to claim 1, wherein the viral diseases are viral hepatitis (A, B, C, E), influenza, viral encephalitis, viral enteritis or viral pericarditis.

12. The method as claimed in claim 1, wherein the animal is a human being.

13. A method for ameliorating or preventing cellular damage in animals caused by viruses, which comprises administering to said animal in need thereof an effective amount of the angiotensin II antagonist compound as an active ingredient and a pharmaceutically acceptable carrier, wherein said angiotensin II antagonist compound is a compound of the formula:

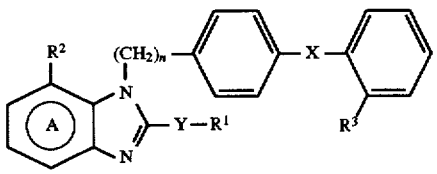

wherein the ring A represents a benzene ring optionally having at least one substituent in addition to $R^2$; $R^1$ represents a hydrogen atom or a hydrocarbon residue which may be substituted; $R^3$ represents a group capable of forming or transformable to an anion; X signifies that the phenylene group and phenyl group are joined to each other either directly or through a spacer comprising a chain of not more than 2 spacer atoms; $R^2$ represents a carboxyl group which may be esterified; Y represents a bond, —O—, —S(O)$_m$— where m represents 0, 1 or 2, or —N($R^4$)— where $R^4$ represents a hydrogen atom or an alkyl group which may be substituted; and n represents a whole number of 1 or 2.

14. A method for ameliorating cellular damage in an animal caused by viruses, which comprises administering to said animal in need thereof an effective amount of (±)-1-(cyclohexyloxycarbonyloxy)ethyl 2-ethoxy-1-[[2'-(1H-tetrazol-5-yl)biphenyl-4-yl]methyl]-1H-benzimidazole-7-carboxylate or a salt thereof as an active ingredient and a pharmaceutically acceptable carrier.

* * * * *

UNITED STATES PATENT AND TRADEMARK OFFICE
CERTIFICATE OF CORRECTION

PATENT NO. : 5,750,551
DATED : May 12, 1998
INVENTOR(S) : Akira Matsumori

It is certified that error appears in the above-identified patent and that said Letters Patent is hereby corrected as shown below:

Title page, ite [*]  Notice, delete "5,105,919" and insert --5,605,919--.

Signed and Sealed this

Twentieth Day of October, 1998

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,750,551
DATED : May 12, 1998
INVENTOR(S) : Akira MATSUMORI

It is certified that error appears in the above-identified patent and that said Letters Patent is hereby corrected as shown below:

On the title page, Item [22] Filed Date is incorrect, delete "Dec. 24, 1996" and insert --Oct. 24, 1996--. Also, Column 20, line 13, delete "1,2,4oxadiazol-3yl) biphenyl" and insert --1,2,4-oxadiazol-3-yl)biphenyl--.

Signed and Sealed this

Eighteenth Day of January, 2000

Attest:

Q. TODD DICKINSON

*Attesting Officer*   *Commissioner of Patents and Trademarks*